(12) United States Patent
Casara et al.

(10) Patent No.: US 6,638,962 B2
(45) Date of Patent: Oct. 28, 2003

(54) CYCLOHEPTENE COMPOUNDS

(75) Inventors: Patrick Casara, Villennes sur Seine (FR); Thierry Le Diguarher, Rueil Malmaison (FR); Gilbert Dorey, Versailles (FR); John Hickman, Puteaux (FR); Alain Pierre, Les Alluets le Roi (FR); Gordon Tucker, Paris (FR); Nicolas Guilbaud, La Celle Saint Cloud (FR)

(73) Assignee: Les Laboratoires Servier, Neuilly-Sur-Seine (FR)

( * ) Notice: Subject to any disclaimer, the term of this patent is extended or adjusted under 35 U.S.C. 154(b) by 0 days.

(21) Appl. No.: 10/050,666

(22) Filed: Jan. 16, 2002

(65) Prior Publication Data

US 2002/0156113 A1 Oct. 24, 2002

(30) Foreign Application Priority Data

Jan. 18, 2001 (FR) .............................. 01.00641

(51) Int. Cl.⁷ .................. A61K 31/4174; C07D 233/64
(52) U.S. Cl. .................. 514/400; 514/357; 546/330; 546/334; 546/329; 548/336.1; 548/335.5; 548/339.5; 548/340.1
(58) Field of Search ............... 548/336.1, 335.5, 548/339.5, 340.1; 546/330, 334, 329; 514/357, 400

(56) References Cited

U.S. PATENT DOCUMENTS

| 5,922,883 A | 7/1999 | Hutchinson |
| 6,028,201 A | 2/2000 | Dinsmore et al. |

FOREIGN PATENT DOCUMENTS

| WO | 96 30343 A | 10/1996 |
| WO | 96 37204 A | 11/1996 |
| WO | 97 36606 A | 10/1997 |
| WO | 97 36890 A | 10/1997 |
| WO | 97 36898 A | 10/1997 |
| WO | 97 38665 A | 10/1997 |
| WO | 99 10329 A | 3/1999 |
| WO | 99 20612 A | 4/1999 |

OTHER PUBLICATIONS

Balci et al., CA 99:175326, 1983.*

* cited by examiner

Primary Examiner—Laura L. Stockton
(74) Attorney, Agent, or Firm—The Firm of Hueschen and Sage

(57) ABSTRACT

Compound of formula (I):

wherein:
X represents a bond or alkylene, CO, $S(O)_n$, $—S(O)_n—A_1—$, $—CO—A_1—$, $—A—S(O)_n—A'_1—$ or $—A_1—CO—A'_1—$, Y represents aryl, heteroaryl, cycloalkyl or heterocycloalkyl, each unsubstituted or substituted, $R_1$, $R_2$, $R_3$ and $R_4$ each independently of the others represent hydrogen or aryl, heteroaryl, cycloalkyl or heterocycloalkyl, each unsubstituted or substituted, or $R_1$, $R_2$, $R_3$ and $R_4$, taken in pairs, together form a bond, or form a fused benzene ring or a fused aromatic or partially unsaturated heterocycle, T represents $—CH(R_5)—$, $—N(R_5)—$ or $—N(R_5)CO—$, V represents hydrogen or unsubstituted or substituted aryl or heteroaryl, $A_2$ represents $[C(R_6)(R'_6)]_p$, $R_7$ and $R_8$ are as defined in the description, their isomers and addition salts thereof with a pharmaceutically acceptable acid or base and medicinal products containing the same are useful as farnesyl transferase inhibitors.

21 Claims, No Drawings

CYCLOHEPTENE COMPOUNDS

SUMMARY OF THE INVENTION

The present invention relates to new cycloheptene compounds, to a process for their preparation and to pharmaceutical compositions containing them.

The compounds of the invention are useful as farnesyl transferase inhibitors.

DESCRIPTION OF THE PRIOR ART

A large number of proteins are subject to post-translational changes which alter their localisation and their function. In particular, lipid-type modifications allow certain proteins that are inactive in their free form to be anchored in the plasma membrane, which is a crucial step for ensuring their function. This applies to prenylation (*Curr. Opin. Cell. Biol.*, 4, 1992, 1008–1016), which is catalysed by several enzymes: farnesyl transferase (FTase) and the two geranylgeranyl transferases (GGTase-I and GGTase-II) which couple a prenyl group to 15 (trans,trans-farnesyl) or 20 (all-trans-geranylgeranyl) carbons on the carboxy terminal moiety of substrate proteins (*J. Biol. Chem.*, 271, 1996, 5289–5292; *Curr. Opin. Struct. Biol.*, 7, 1997, 873–880). FTase catalyses that transfer, starting from farnesyl pyrophosphate, to form a thio ether bond on the cysteine of the terminal tetrapeptide consensus sequence $CA_1A_2X$ found on substrate proteins, C denoting cysteine, $A_1$ and $A_2$ denoting an aliphatic amino acid and X denoting a serine, an alanine or a methionine. GGTase-I uses geranylgeranyl pyrophosphate as donor substrate for effecting a similar transfer, but this time the consensus sequence CAAX is terminated by a leucine or a phenylalanine. Those two heterodimeric enzymes share an alpha subunit of 48 kDa, and possess two distinct beta chains, although they have 30% homology of amino acid sequences. GGTase-II acts on terminal sequences of the XXCC and XCXC types and has alpha and beta subunits different from those of the aforementioned enzymes.

The interest in inhibiting one of those enzymes, FTase, is based on the implication in tumour progression of the prenylated oncogene Ras (*Annu. Rev. Biochem.*, 56, 1987, 779–827). Ras proteins exist in four major forms, Harvey or H-Ras, N-Ras, and Kirsten or K-Ras A and B. Those proteins are expressed in a mutated form in at least a quarter of cancers with an even greater incidence for some histological types of tumour and according to the form of Ras. For example, mutations of K-Ras B are found in 80 to 90% of pancreatic carcinomas and 30 to 60% of colon cancers (*Int. J. Oncol.*, 7, 1995, 413–421). Numerous preclinical data have demonstrated the role of that oncogene in tumour progression, more especially in cell growth phenomena. It is an essential link in the transmission of extracellular signals—such as those activated by growth factors—to diverse cytosolic kinases and then to the nucleus, for integration in terms of proliferation, cell death and cell survival (*Cancer Met. Rev.*, 13, 1994, 67–89; *Curr. Opin. Genetics & Develop.*, 8, 1998, 49–54; *J. Biol. Chem.* 273, 1998, 19925–19928), or of regulation with the tumour environment—angiogenesis in particular (*Cancer Res.*, 55, 1995, 4575–4580).

BACKGROUND OF THE INVENTION

The search for FTase inhibitors is thus of considerable interest in oncology (*Curr. Opin. Chem. Biol.*, 2, 1998, 40–48). As 0.5% of animal proteins are probably prenylated and in the majority geranylgeranylated, specific inhibitors of FTase relative to the GGTases, and more especially GGTase-I, which is similar in structure to FTase, are of considerable interest. The first work with such inhibitors, peptidomimetic analogues of the farnesylation consensus sequence, and the following work with molecules obtained by chemical library screening, confirmed the anti-tumour strategy in in vitro and animal experiments (*Annu. Rev. Pharmacol. Toxicol.*, 37, 1997, 143–166; *Biochim. Biophys. Acta,* 1423, 1999, C19–C30; *Cancer Res.*, 58, 1998, 4947–4956). Fibroblasts specially transfected with the mutated H-Ras protein gene and implanted in an animal develop a tumour mass the growth of which is reduced as a function of the dose of FTase inhibitor received by the animal. In the case of transgenic animals that express a mutated form of H-Ras under the control of an appropriate promoter causing the random appearance of spontaneous mammary or salivary tumours, those same inhibitors bring about the regression of established tumours and block the appearance of new ones for the duration of the treatment. Finally, such products are also active in reducing the growth of human xenotransplants in the mouse, with a possible effect of increasing survival, depending on the model. The mutated Ras protein is not the only indirect target of those inhibitors in tumour pathology. The study of multiple tumour models has enabled confirmation of inhibition of tumour growth independently of the presence of mutated Ras proteins. That effect could be partly associated with a direct antiangiogenic activity and thus could be independent of the oncogenic profile of the tumour (*Eur. J. Cancer*, 35, 1999, 1394–1401). This observation reinforces and increases the potential for anti-tumour use of that class of inhibitors, and the absence of debilitating side effects on normal cell functions is also favourable for the inhibition of FTase in any pathology associated with mechanisms changed or amplified by a farnesylated protein or by farnesylated proteins. Aside from cancer, this applies especially, for example, to restenosis following angioplasty or vascular surgery, and to type I neurofibromatosis (*Mol. Cell. Biol.*, 17, 1997, 862–872).

The compounds of the invention have a novel structure and are capable of selective inhibition of FTase relative to the GGTases. They will accordingly be useful in the treatment of all pathologies associated with intracellular signalling through Ras proteins or other farnesylated proteins, and in pathologies associated with angiogenesis amplification. They will thus be of use in the treatment of cancer, but also in the treatment of restenosis following angioplasty or vascular surgery, and in the treatment of type I neurofibromatosis.

DETAILED DESCRIPTION OF THE INVENTION

The present invention relates to compounds of formula (I):

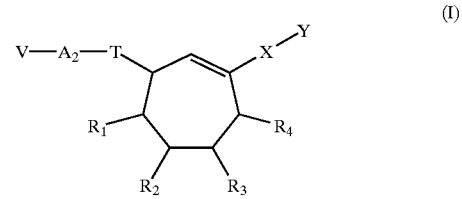

wherein:

X represents a bond or a group selected from alkylene, CO, $S(O)_n$, *—$S(O)_n$—$A_1$—, *—CO—$A_1$—, —$A_1$—$S(O)_n$—$A'_1$— and —$A_1$—CO—$A'_1$— (wherein $A_1$ and $A'_1$, identical or different, represent an alkylene group and n is 0, 1 or 2), the symbol "*" indicating the point of attachment of those groups to the cycloheptene, Y represents an aryl, heteroaryl, cycloalkyl or heterocycloalkyl group, each of those groups being unsubstituted or substituted by one or more, identical or different, $R_8$ groups, $R_1$, $R_2$, $R_3$ and $R_4$ each independently of the others represent a hydrogen atom or an aryl, heteroaryl, cycloalkyl or heterocycloalkyl group, each of those groups being unsubstituted or substituted by one or more, identical or different, $R_8$ groups, or $R_1$, $R_2$, $R_3$ and $R_4$, taken in pairs, together form a bond, or $R_1$ and $R_2$, or $R_2$ and $R_3$, or $R_3$ and $R_4$, taken in pairs with the carbon atoms to which they are bonded, form a fused benzene ring or a fused aromatic or partially unsaturated heterocycle, having 5 or 6 ring members and containing 1 or 2 hetero atoms selected from nitrogen, oxygen and sulphur, on the understanding that only one ring can be fused on the 7-membered structure, T represents a —CH($R_5$)—, —N($R_5$)— or *—N($R_5$)CO— group (wherein $R_5$ represents a hydrogen atom or an alkyl, aryl, heteroaryl, arylalkyl or heteroarylalkyl group, each of those groups being unsubstituted or substituted by one or more, identical or different, $R_7$ groups), the symbol "*" indicating the point of attachment of the group to the cycloheptene, V represents a hydrogen atom or an aryl or heteroaryl group, each of those groups being unsubstituted or substituted by one or more, identical or different, $R_7$ groups, $A_2$ represents a $[C(R_6)(R'_6)]_p$ group wherein p is 0, 1, 2, 3 or 4 when T represents a —CH($R_5$)— or *—N($R_5$)CO— group, or p is 1, 2, 3 or 4 when T represents an —N($R_5$)— group; and $R_6$ and $R'_6$, which may be identical or different, represent a hydrogen atom or an alkyl, alkenyl, alkynyl, optionally substituted aryl, optionally substituted heteroaryl, optionally substituted heterocycloalkyl, optionally substituted arylalkyl, optionally substituted heteroarylalkyl or optionally substituted heterocycloalkylalkyl group, an $R_9$ group or an alkyl group substituted by an $R_9$ group (wherein $R_9$ represents an —$OR_5$, —N($R_5$)($R'_5$), —$S(O)_mR_5$, —CON($R_5$)($R'_5$), —N($R_5$)$COR'_5$, —N($R_5$)$SO_2R'_5$, —$SO_2N(R_5)(R'_5)$ or —N($R_5$)$COO(R'_5)$ group, m being 0, 1 or 2, and $R'_5$ can have any of the meanings of $R_5$), $R_7$ represents a halogen atom or an alkyl, alkoxy, hydroxy, mercapto, alkylthio, cyano, amino (optionally substituted by one or two alkyl groups), nitro, carboxy, alkoxycarbonyl, aminocarbonyl (optionally substituted by one or two alkyl groups), carbamoyl, unsubstituted or substituted aryl, unsubstituted or substituted arylalkyl, unsubstituted or substituted heteroaryl, unsubstituted or substituted heteroarylalkyl, unsubstituted or substituted cycloalkyl, unsubstituted or substituted cycloalkylalkyl, unsubstituted or substituted heterocycloalkyl or unsubstituted or substituted heterocycloalkylalkyl group, $R_8$ represents a halogen atom, or an oxo, hydroxy, cyano, nitro, carboxy, alkoxycarbonyl or perhaloalkyl group or a —U—$R_{80}$ or —$A_{80}$—U—$R_{80}$ group (wherein $A_{80}$ represents an alkylene group; U represents a bond, an oxygen atom or a group selected from NH, $S(O)_m$, NHCO, CONH, $SO_2NH$ and $NHSO_2$, m being 0, 1 or 2; and $R_{80}$ is a group selected from alkyl, aryl, arylalkyl, heteroaryl and heteroarylalkyl), it being understood that:

the term "alkyl" denotes a linear or branched group containing from 1 to 6 carbon atoms, the term "alkylene" denotes a linear or branched bivalent group containing from 1 to 6 carbon atoms, the term "cycloalkyl" denotes a saturated cyclic group containing from 3 to 8 carbon atoms, the term "heterocycloalkyl" denotes a saturated or partially unsaturated cyclic group having from 5 to 7 ring members and containing from 1 to 3 hetero atoms selected from nitrogen, oxygen and sulphur, the term "aryl" denotes a phenyl or naphthyl group, the term "heteroaryl" denotes a mono- or bi-cyclic group that is aromatic or contains at least one aromatic ring, has from 5 to 11 ring members and contains from 1 to 5 hetero atoms selected from nitrogen, oxygen and sulphur, the term "substituted" applied to the terms "aryl", "heteroaryl", "cycloalkyl" and "heterocycloalkyl" means that those groups may be substituted by one or more identical or different groups selected from cyano, alkylcarbonyl, aminocarbonyl (optionally substituted by one or two alkyl groups) and halogen atoms, the term "substituted" applied to the terms "arylalkyl", "heteroarylalkyl", "cycloalkylalkyl" and "heterocycloalkylalkyl" means that the cyclic moiety of those groups may be substituted by one or more identical or different groups selected from oxo, cyano, alkylcarbonyl, aminocarbonyl (optionally substituted by one or two alkyl groups) and halogen atoms, their enantiomers, diastereoisomers, and addition salts thereof with a pharmaceutically acceptable acid or base.

Among the pharmaceutically acceptable acids there may be mentioned hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, etc.

Among the pharmaceutically acceptable bases there may be mentioned sodium hydroxide, potassium hydroxide, triethylamine, tert-butylamine, etc.

In the compounds of formula (I), X preferably represents a bond.

Preferred compounds of formula (I) are those wherein Y represents an aryl group (preferably phenyl optionally substituted by $R_8$).

An advantageous aspect of the invention relates to compounds of formula (I) wherein each of $R_1$, $R_2$, $R_3$ and $R_4$ represents a hydrogen atom.

More especially, the invention relates to compounds of formula (I) wherein T represents an —N($R_5$)— group and, more especially still, an —NH— group.

Preferred $A_2$ groups are the groups methylene, ethylene, (4-cyanophenyl)methylene, (4-chlorophenyl)methylene, (4-cyanobenzyl)methylene and (4-chlorobenzyl)methylene.

Very advantageously, V represents a heteroaryl group, such as, for example, the groups pyridyl and 1H-imidazolyl, those groups preferably being substituted by an optionally substituted arylalkyl group, such as, for example, the group p-cyanobenzyl or p-chlorobenzyl.

The preferred V—$A_2$—T— group of the invention is the group [(4-cyanobenzyl)-1H-imidazol-5-yl]methylamino.

In the preferred compounds of formula (I) when V is substituted by $R_7$, $R_7$ represents an optionally substituted arylalkyl or optionally substituted heteroarylalkyl group. Those groups are advantageously substituted by a halogen atom or by a cyano group. An especially advantageous aspect of the invention relates to compounds of formula (I) wherein X represents a bond, Y represents an aryl group optionally substituted by $R_8$, each of $R_1$, $R_2$, $R_3$ and $R_4$ represents a hydrogen atom, T represents an —N($R_5$)— group and more especially still an —NH— group, $A_2$ represents a —$CH_2$—, —$CH_2$—$CH_2$—, (4-cyanophenyl)methylene, (4-chlorophenyl)methylene, (4-cyanobenzyl)methylene or (4-chlorobenzyl)methylene group and V represents a heteroaryl group, such as, for example, the groups pyridyl and 1H-imidazolyl optionally substituted by $R_7$.

Among the preferred compounds of formula (I), there may be mentioned more especially: 4-{[5-({[3-(2-methylphenyl)-2-cyclohepten-1-yl]amino}methyl)-1H-imidazol-1-yl]-methyl}benzonitrile, 4-{[5-({[3-(3-methylphenyl)-2-cyclohepten-1-yl]amino}methyl)-1H-imidazol-1-yl]methyl}benzonitrile and 4-{[5-({[3-(3-chlorophenyl)-2-cyclohepten-1-yl]amino}methyl)-1H-imidazol-1-yl]methyl}benzonitrile.

The present invention relates also to a process for the preparation of compounds of formula (I), characterised in that there is used as starting material a compound of formula (II):

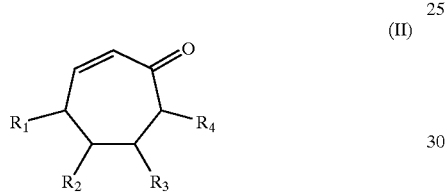

(II)

wherein $R_1$, $R_2$, $R_3$ and $R_4$ are as defined for formula (I), the carbonyl function of which reacts with an organometallic compound of formula Li—X—Y wherein X and Y are as defined for formula (I), to yield a compound of formula (III):

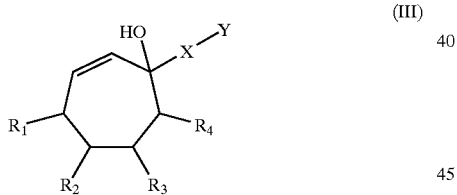

(III)

wherein $R_1$, $R_2$, $R_3$, $R_4$, X and Y are as defined hereinbefore, which is subjected to an isomerisation reaction in an acidic medium, to yield a compound of formula (IV):

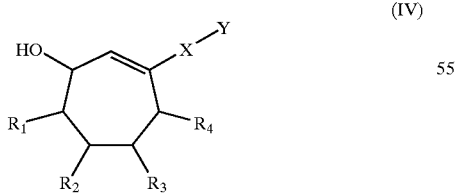

(IV)

wherein $R_1$, $R_2$, $R_3$, $R_4$, X and Y are as defined hereinbefore, which compound of formula (IV), after conversion of the hydroxyl function to a leaving group, is subjected to:

the introduction of a reactive function by the action of a silyl compound, such as $Me_3SiCN$, $CH_2=CH-CH_2-$ $SiMe_3$ or $CH_2=C(Oalk)(OSiMe_3)$ wherein alk represents an alkyl group, and then to condensation of the appropriate groups to yield a compound of formula (I/a)

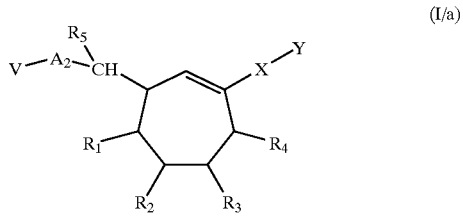

(I/a)

a particular case of the compounds of formula (I) wherein $R_1$, $R_2$, $R_3$, $R_4$, $R_5$, $A_2$, V, X and Y are as defined hereinbefore, or the action of sodium azide, to yield, after hydrolysis in the presence of triphenylphosphine, an amine of formula (V):

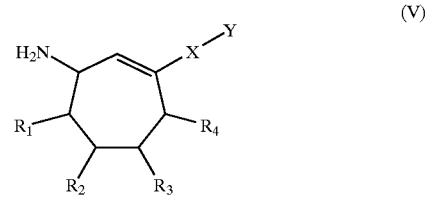

(V)

wherein $R_1$, $R_2$, $R_3$, $R_4$, X and Y are as defined hereinbefore, which compound of formula (V) is condensed with an aldehyde of formula:

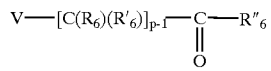

wherein V is as defined hereinbefore, $R_6$ and $R'_6$ are as defined for formula (I), $R''_6$ represents the same atoms or groups as those defined for $R_6$ or $R'_6$, and p is 1, 2, 3 or 4, to yield a compound of formula (I/b):

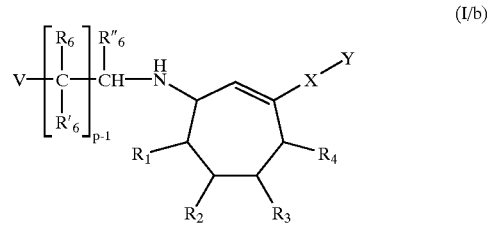

(I/b)

a particular case of the compounds of formula (I) wherein $R_1$, $R_2$, $R_3$, $R_4$, $R_6$, $R'_6$, $R''_6$, V, X, Y and p are as defined hereinbefore,

[certain compounds of formula (I/b) may also be obtained starting from the compound of formula (II'):

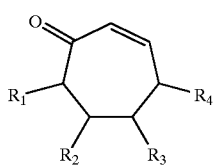

wherein $R_1$, $R_2$, $R_3$ and $R_4$ are as defined hereinbefore, which, after the formation of the corresponding silyl ether, is subjected to the action, in a strong basic medium, of a compound Y—X'—CHO wherein Y is as defined hereinbefore and X' represents a bond or an alkylene group, to yield, after deprotection, a compound of formula (III'):

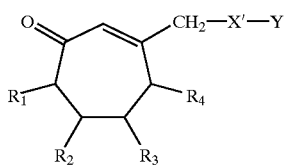

wherein $R_1$, $R_2$, $R_3$, $R_4$, X' and Y are as defined hereinbefore,
which is condensed with an amine of formula V—$A_2$—$NH_2$ wherein V and $A_2$ are as defined hereinbefore, to obtain a compound of formula (I/$b_a$), a particular case of the compounds of formula (I/b):

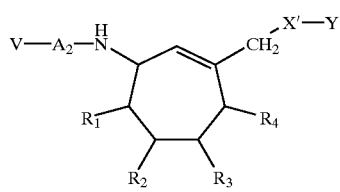

wherein $R_1$, $R_2$, $R_3$, $R_4$, V, $A_2$, X' and Y are as defined hereinbefore],
or which compound of formula (V) is subjected to an acylation reaction with a compound of formula V—$A_2$—CO-Hal wherein V and $A_2$ are as defined for formula (I) and Hal represents a halogen atom, or to coupling with a carboxylic acid of formula V—$A_2$-COOH wherein V and $A_2$ are as defined for formula (I), to yield a compound of formula (I'/b):

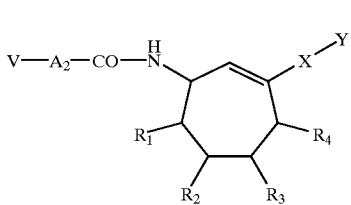

wherein $R_1$, $R_2$, $R_3$, $R_4$, $A_2$, V, X and Y are as defined hereinbefore,
which compounds (I/b) and (I'/b) may be subjected to the same type of condensation as before, with an aldehyde of formula R"$_5$CHO, or with an acyl halide of formula R"$_5$—CO-Hal, or with a carboxylic acid of formula R"$_5$—COOH, wherein R"$_5$ can have any of the meanings of $R_5$ with the exception of a hydrogen atom, to yield a compound of formula (I/c):

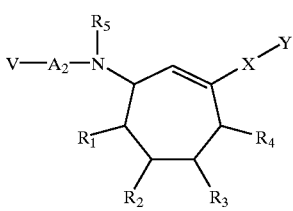

a particular case of the compounds of formula (I) wherein $R_1$, $R_2$, $R_3$, $R_4$, $R_5$, $A_2$, V, X and Y are as defined hereinbefore,
which compounds of formulae (I/a), (I/b), (I'/b) and (I/c) constitute the totality of the compounds of formula (I),
which may, if necessary, be purified according to a conventional purification technique,
are separated, where appropriate, into their isomers according to a conventional separation technique,
which are converted, if desired, into addition salts thereof with a pharmaceutically acceptable acid or base.

The present invention relates also to pharmaceutical compositions comprising as active ingredient at least one compound of formula (I), alone or in combination with one or more inert, non-toxic, pharmaceutically acceptable excipients or carriers.

Among the pharmaceutical compositions according to the invention, there may be mentioned more especially those that are suitable for oral, parenteral, nasal or transdermal administration, tablets or dragees, sublingual tablets, gelatin capsules, lozenges, suppositories, creams, ointments, dermal gels, etc.

The useful dosage varies according to the age and weight of the patient, the nature and severity of the disorder and the route of administration, which may be oral, nasal, rectal or parenteral. Generally, the unit dose ranges from 0.05 to 500 mg per 24 hours for a treatment in from 1 to 3 administrations.

The following Examples illustrate the invention but do not limit it in any way. The structures of the compounds described were confirmed by the usual spectroscopic techniques.

The starting materials used are known products or are prepared according to known procedures.

Preparation 1: 4-[(5-Formyl-1H-imidazol-1-yl) methyl]benzonitrile

Step A: 4-{[5-(Hydroxymethyl)-1H-imidazol-1-yl] methyl}benzonitrile

Dihydroxyacetone in dimeric form (23.35 g/0.129 mol) and potassium thioisocyanate (25.18 g/0.259 mol) are added in succession to a solution of 25 g (0.233 mol) of 4-(aminomethyl)benzonitrile in 100 ml of isopropanol, and then the mixture is placed in an ice bath and 20 ml of acetic acid are added dropwise. The reaction mixture is stirred at room temperature for 48 hours. A precipitate is obtained, which is filtered off, washed with 50 ml of isopropanol and then twice with 50 ml of $H_2O$, and subsequently dried. Thus crystals are obtained, which are used directly in the following desulphurisation step: 13 g (0.059 mol) of the previously obtained crystals are placed in 140 ml of a dilute solution of 10% nitric acid in water. At 0° C., 0.1 g of sodium nitrite is added very slowly. Marked evolution of a brown gas is observed, and the mixture gradually becomes homogeneous. The reaction mixture is then stirred at room temperature for 3 hours and then filtered and extracted once with AcOEt. The aqueous phase is then rendered basic with a 5N sodium hydroxide solution, and subsequently extracted twice with AcOEt. The organic phase is washed with a saturated NaCl solution, and then dried over $MgSO_4$. Evaporation in vacuo yields the title product.

Step B: 4-[(5-Formyl-1H-imidazol-1-yl)methyl] benzonitrile

Triethylamine (13.8 ml/99.6 mmol) and then $SO_3$-pyridine complex (9.89 g/62.25 mmol) are added in succession to a solution of 4.6 g (24.9 mmol) of the compound obtained in Step A in 120 ml of DMSO, and the reaction mixture is stirred at room temperature for 30 minutes. The whole is then brought to 0° C., hydrolysed with $H_2O$, and then extracted several times with AcOEt. The organic phases are combined, washed with a saturated NaCl solution, dried over $MgSO_4$, and evaporated to dryness to yield the title product.

Preparation 2: 4-{[5-(Aminomethyl)-1H-imidazol-1-yl]methyl}benzonitrile 3.83 g (49.7 mmol) of ammonium acetate and $NaBH_3CN$ (0.313 g/4.97 mmol) are added to a solution of the compound obtained in Preparation 1 (1.05 g/4.97 mmol) in 50 ml of methanol, and the whole is stirred at room temperature for 48 hours. The reaction mixture is then hydrolysed with a saturated $NaHCO_3$ solution, and extracted with AcOEt. The organic extracts are then combined, dried over $MgSO_4$ and concentrated to dryness. The residual oil is then purified over a column of silica gel ($CH_2Cl_2$, MeOH, $NH_4OH$, 98/1.5/0.5) to yield the title product in the form of a white foam.

Preparations 3 to 13 are obtained according to the same process as in Preparations 1 and 2, replacing 4-(aminomethyl)benzonitrile by the appropriate substrate:

Preparation 3: 4-[1-(5-Formyl-1H-imidazol-1-yl) ethyl]benzonitrile

Preparation 4: 4-[(5-Formyl-1H-imidazol-1-yl) methyl]cyclohexanecarbonitrile

Preparation 5: 1-[(1-Cyano-4-piperidyl)methyl]-1H-imidazole-5-carbaldehyde

Preparation 6: 1-(3-Phenylpropyl)-1H-imidazole-5-carbaldehyde

Preparation 7: 1-(4-Fluorobenzyl)-1H-imidazole-5-carbaldehyde

Preparation 8: 1-(4-Chlorobenzyl)-1H-imidazole-5-carbaldehyde

Preparation 9: 1-(3-Chlorobenzyl)-1H-imidazole-5-carbaldehyde

Preparation 10: 1-(4-Bromophenyl)-1H-imidazole-5-carbaldehyde

Preparation 11: 1-Benzyl-1H-imidazole-5-carbaldehyde

Preparation 12: 4-{[5-(2-Oxoethyl)-1H-imidazol-1-yl]methyl}benzonitrile

Preparation 13: 1-(2-Phenylethyl)-1H-imidazole-5-carbaldehyde

Preparation 14: 4-[(3-Formyl-4-pyridyl)methyl] benzonitrile

Step A: Phenyl 4-(4-cyanobenzyl)-3-formyl-1(4H)-pyridinecarboxylate

A solution of 4-bromobenzonitrile in solution in 20 ml of THF is added dropwise to a suspension of 1.44 g (0.022 mol) of zinc in 20 ml of anhydrous THF that has been brought to −20° C. The whole is stirred at room temperature for 4 hours.

In parallel, 3-pyridinecarboxaldehyde (1.9 ml/0.02 mol) is brought to solution in 20 ml of anhydrous THF and then, at 0° C., phenyl chloroformate (2.5 ml/0.02 mol) in solution in 10 ml of THF is added, and the reaction mixture is stirred at that temperature for 1 hour. A whitish precipitate is seen to form.

The previously obtained bromo-zinc compound is then transferred into the protected pyridine, and the whole is stirred at 0° C. for 1.5 hours, and subsequently allowed to return gradually to room temperature and stirred for 1.5 hours at that temperature. Hydrolysis is carried out using a saturated $NH_4Cl$ solution, extraction is carried out with AcOEt, and the extract is washed with a saturated NaCl solution, followed by drying over $MgSO_4$ and then evaporation to dryness. A brown oil is obtained, which is purified by chromatography over silica gel (heptane, 10% AcOEt) to obtain the title product.

Step B: 4-[(3-Formyl-4-pyridyl)methyl]benzonitrile

The product obtained in Step A (2 g/0.0058 mol) is brought to solution in 80 ml of Decalin, and then 0.336 g (0.010 mol) of sulphur is added, and the whole is heated at 140–150° C. for 24 hours. The reaction mixture is filtered and then concentrated. A brown oil is obtained, which is purified by chromatography over silica gel (heptane, 10% AcOEt 10%) to yield the title product.

Elemental Microanalysis

|  | C % | H % | N % |
|---|---|---|---|
| Theory: | 75.65 | 4.53 | 12.60 |
| Found: | 75.50 | 4.32 | 12.50 |

Preparation 15: 4-[(Imidazol-4-yl)-carbonyl] benzonitrile

Step A: N,N-Dimethyl-1H-imidazole-1-sulphonamide

This compound is prepared according to the protocol described by D. J. Chadwick and R. I. Ngochindo, J. Chem. Soc., Perkin Trans., 481, 1984, starting from 10.2 g (0.15 mol) of imidazole, 20 g of a translucent yellow oil are obtained, which crystallises gradually at room temperature in the form of an amorphous solid in a yield of 93%. IR 1177 and 1391 $cm^{-1}$, ν ($NSO_2$). NMR ($CDCl_3$): 7.35, d, (1H); 7.25 d, (1H); 7.15 s, (1H); 2.31 s, (6H).

Elemental Microanalysis

|  | C % | H % | N % | S % |
|---|---|---|---|---|
| Theory: | 34.28 | 5.18 | 23.98 | 18.30 |
| Found: | 34.71 | 5.53 | 23.02 | 18.47 |

Step B: 2-[tert-Butyl(dimethyl)silyl]-N,N-dimethyl-1H-imidazole-1-sulphonamide

This compound is prepared according to the protocol described by J. W. Kim, S. M. Abdelaal and L. Bauer J. Heterocyclic Chem., 611 1995, by lithiation of the compound obtained in Step B with n-butyllithium (1.6M solution in hexane) at −78° C., followed by the addition of TBDMSiCl. After chromatography over silica gel (ethyl acetate in heptane), 2-[tert-butyl(dimethyl)silyl]-N,N-dimethyl-1H-imidazole-1-sulphonamide is isolated in a yield of 80% in the form of a translucent yellow oil. IR 1176 and 1386 cm$^{-1}$, ν (NSO$_2$). NMR (CDCl$_3$): 7.35, d, (1H); 7.25 d, (1H); 2.85, s, (6H); 1.0 s, (9H); 0.45, s, (6H).

Step C: 2-[tert-Butyl(dimethyl)silyl]-5-[(4-cyanophenyl)(hydroxy)methyl]-N,N-dimethyl-1H-imidazole-1-sulphonamide 12.5 ml (19.9 mmol) of a solution of n-butyllithium (1.6M solution in hexane) are added slowly to a solution of the compound obtained in Step B (4.67 g, 18 mmol) in 40 ml of anhydrous THF that has been brought to −78° C., and then the whole is maintained at that temperature for 1 hour 30 minutes. A solution of p-cyanobenzaldehyde in 20 ml of THF, 3.3 g (25.1 mmol) is then added. The whole is stirred at −78° C. for 0.5 hour, and then hydrolysed with an aqueous saturated NaHCO$_3$ solution. When the reaction mixture is at room temperature, it is extracted with AcOEt and then washed with a saturated NaCl solution, dried over MgSO$_4$ and concentrated to dryness.

After purification over silica gel (heptane/AcOEt 3/1), 5.8 g of the title product are obtained in a yield of 83%. IR: 3449 ν (OH); 2230 ν(CN); 1609 ν(C═C); 1376 and 1146 ν cm$^{-1}$ (NSO$_2$). NMR (CDCl$_3$): 7.7, d, (2H); 7.6 d, (2H); 6.65 s (1H); 6.15 s (1H); 3.35 m (1H, OH); 2.85, s, (6H); 1.0 s, (9H); 0.45, s, (6H).

Step D: 5-[(4-Cyanophenyl)(hydroxy)methyl]-N,N-dimethyl-1H-imidazole-1-sulphonamide The compound obtained in Step C (4 g, 9.5 mmol) is brought to solution in 40 ml of THF. A mixture of AcOH/H$_2$O (7:3) (40 ml) is then added, and the whole is stirred at room temperature for 2 hours. The reaction mixture is then hydrolysed in a mixture of ice and H$_2$O, extracted with AcOEt and washed with a saturated NaHCO$_3$ solution, and then with a saturated NaCl solution, dried over MgSO$_4$ and concentrated to dryness. The residual solid is then triturated in heptane, and the title product is obtained in the form of white crystals, 2.57 g, in a yield of 89%. IR: 3200 2700 ν(OH); 2230 ν(CN); 1390 and 1152 ν cm$^{-1}$ (NSO$_2$). NMR (CDCl$_3$): 7.9, s, (1H); 7.75 and 7.55 2d, (4H); 6.55 s (1H); 6.15 d (1H); 3.25d(1H,OH); 3.0,s,(6H).
Elemental Microanalysis

|  | C % | H % | N % | S % |
| --- | --- | --- | --- | --- |
| Theory: | 50.97 | 4.61 | 18.29 | 10.47 |
| Found: | 51.58 | 4.76 | 18.05 | 10.12 |

Step E: 4-(1H-Imidazol-5-ylcarbonyl)benzonitrile 4-(1H-Imidazol-5-ylcarbonyl)benzonitrile is obtained according to the method described by F. Effenberger; M. Roos; R. Ahmad; and A. Krebs; Chem. Ber.; 124 (7); 1639–1650; 1991, starting from the compound obtained in the preceding Step by oxidation with chromic anhydride in acetic acid at reflux.

Preparation 16: 4-[(1-Methyl-1H-imidazol-5-yl)carbonyl]benzonitrile

Step A: 4-[(1-Trityl-1H-imidazol-5-yl)carbonyl]benzonitrile

The compound obtained in Step E of Preparation 15 is brought to solution in DMF, and 2 molar equivalents of Et$_3$N and 1.1 molar equivalents of triphenylmethyl chloride are added in succession. The whole is stirred at room temperature for 96 hours. The reaction mixture is then hydrolysed in a mixture of H$_2$O and ice, and extracted with AcOEt. After washing with a dilute 1N HCl solution and then with a saturated NaHCO$_3$ solution and finally with a saturated NaCl solution, the reaction mixture is concentrated to dryness and purified over silica gel (heptane, AcOEt). 4-[(1-Trityl-1H-imidazol-5-yl)carbonyl]benzonitrile is obtained in the form of a crystalline compound in a yield of 78%.

Step B: 4-[(1-Methyl-1H-imidazol-5-yl)carbonyl]benzonitrile

This compound is obtained starting from the compound prepared in the preceding Step using the method described by I. M. Bell et al., J. Med. Chem.; .44; 2933–2949 2001, in 2 steps, replacing benzyl bromide by methyl iodide as alkylating agent.

A purification step over silica gel enables 4-[(1-methyl-1H-imidazol-5-yl)carbonyl]-benzonitrile to be isolated.

Preparation 17: 4-[2-(1H-Imidazol-5-yl)-2-oxoethyl]benzonitrile

This compound is obtained according to the same process as for Preparation 15, in Step C using 4-(cyanophenyl)acetaldehyde as alkylating agent instead of p-cyanobenzaldehyde.

Preparation 18: 4-[2-(1-Methyl-1H-imidazol-5-yl)-2-oxoethyl]benzonitrile

This compound is obtained according to the same process as for Preparation 16, using the compound obtained in Preparation 17.

Preparation 19: (4-Chlorophenyl)(1H-imidazol-5-yl)methanone

This compound is obtained according to the same process as in Preparation 15, in Step C using 4-(chlorophenyl)benzaldehyde instead of p-cyanobenzaldehyde as alkylating agent.

Preparation 20: (4-Chlorophenyl)(1-methyl-1H-imidazol-5-yl)methanone

This compound is obtained according to the same process as Preparation 16, using the compound obtained in Preparation 19.

Preparation 21: 2-(4-Chlorophenyl)-1-(1H-imidazol-5-yl)ethanone

This compound is obtained according to the same process as Preparation 15, in Step C using 4-(chlorophenyl)acetaldehyde instead of p-cyanobenzaldehyde as alkylating agent.

Preparation 22: 2-(4-Chlorophenyl)-1-(1-methyl-1H-imidazol-5-yl)ethanone

This compound is obtained according to the same process as Preparation 16, described above, using the compound obtained in Preparation 21.

EXAMPLE 1

4-{[5-({[3-(2-Methylphenyl)-2-cyclohepten-1-yl]amino}methyl)-1H-imidazol-1-yl]methyl}benzonitrile

Step A: 1-(2-Methylphenyl)-2-cyclohepten-1-ol

This compound is obtained by adopting the method described in *Tetrahedron* Vol 52, no. 9, pp 3107–3116, 1996.

16.9 ml (26.9 mmol) of a solution of nBuLi (1.6 M/hexane) are added slowly to a solution of 3.25 ml (26.9 mmol) of α-bromotoluene in a mixture of THF/Et$_2$O (50/25 ml) that has been brought to −78° C. The whole is stirred at that temperature for 30 minutes, and then cycloheptenone (3 ml/26.9 mmol) is added, the mixture is stirred at that temperature for 1 hour and then stirred overnight, the temperature gradually returning to room temperature. The reaction mixture is then hydrolysed in a saturated NaHCO$_3$ solution, and extracted with Et$_2$O. Washing with a saturated NaCl solution, drying over MgSO$_4$ and evaporation to dryness yield a brown oil which is purified by chromatography over silica gel (heptane, 2% AcOEt) to yield the title product in the form of a colourless oil.

Elemental Microanalysis

|  | C % | H % |
|---|---|---|
| Theory: | 83.12 | 8.97 |
| Found: | 83.26 | 8.75 |

Step B: 3-(2-Methylphenyl)-2-cyclohepten-1-ol

A dilute solution of 1% concentrated H$_2$SO$_4$ in H$_2$O (100 ml) is added dropwise to a solution of the compound obtained in Step A (3.7 g/18.29 mmol) in 100 ml of dioxane. The whole is then stirred at room temperature for 2 hours. The reaction mixture is extracted with Et$_2$O, and washed with a saturated NaHCO$_3$ solution and then with a saturated NaCl solution until neutral. Drying over MgSO$_4$ and evaporation to dryness yield an oil, which is purified by chromatography over silica gel (heptane, AcOEt, 4/1) to yield the title product in the form of a colourless oil.

Elemental Microanalysis

|  | C % | H % |
|---|---|---|
| Theory: | 83.12 | 8.97 |
| Found: | 83.70 | 8.77 |

Step C: 3-(2-Methylphenyl)-2-cyclohepten-1-yl acetate

To a solution of the compound obtained in Step B (6.2 g/0.03 mol) in 100 ml of CH$_2$Cl$_2$ there are added, in succession, pyridine (4.9 ml/0.06 mol), DMAP (1.83 g/0.015 mol), and then, dropwise, acetic anhydride (5.7 ml/0.06 mol). The whole is then stirred at room temperature for 24 hours. The reaction mixture is then concentrated to dryness, taken up in AcOEt, washed with a dilute HCl solution (1N), a saturated NaHCO$_3$ solution and then with a saturated NaCl solution; dried over MgSO$_4$ and then concentrated to dryness. The residual yellowish oil is then purified by chromatography over silica gel to yield the title product in the form of white crystals.

Step D: 3-Azido-1-(2-methylphenyl)-1-cycloheptene

To a solution of the compound obtained in Step C (3.52 g/14.65 mmol) in 50 ml of 1,2-dichloroethane there are added dropwise trimethylsilyl azide (TMSN$_3$), and then 0.326 g (1.46 mmol) of magnesium perchlorate (Mg(ClO$_4$)$_2$), and the whole is stirred at room temperature overnight. Hydrolysis is then carried out using H$_2$O, followed by extraction with AcOEt; the organic phases are then combined, washed with a saturated NaCl solution, dried over MgSO$_4$ and concentrated to dryness. The yellow oil so obtained is chromatographed over a column of silica gel (cyclohexane, 2% AcOEt) to yield the title product in the form of a translucent oil.

Step E: 3-(2-Methylphenyl)-2-cyclohepten-1-ylamine 2.5 ml of H$_2$O and then 4.23 g (16.1 mmol) of triphenylphosphine PPh$_3$ are added to a solution of the compound obtained in Step D (2.4 g/10.73 mmol) in 60 ml of THF, and then the reaction mixture is stirred at room temperature overnight. The whole is then concentrated to dryness and subsequently chromatographed over silica gel (CH$_2$Cl$_2$, 20% MeOH, 2% NH$_4$OH) to yield the title product in the form of a yellowish oil.

Elemental Microanalysis

|  | C % | H % | N % |
|---|---|---|---|
| Theory: | 83.53 | 9.51 | 6.96 |
| Found: | 82.71 | 9.32 | 7.09 |

Step F: 4-{[5-({[3-(2-Methylphenyl)-2-cyclohepten-1-yl]amino}methyl)-1H-imidozal-1-yl]methyl}benzonitrile 0.82 g (3.88 mmol) of the compound obtained in Preparation 1, and then NaHB(OAc)$_3$ (1.18 g/5.55 mmol) are added to a solution of the compound obtained in Step E (0.746 g/3.7 mmol) in 30 ml of C$_2$H$_4$Cl$_2$, and the whole is stirred at room temperature for 48 hours. The reaction mixture is then hydrolysed in water, extracted with AcOEt and then washed to neutrality. After drying over MgSO$_4$ and evaporation to dryness, the residual oil is then purified by chromatography over silica gel with eluant (CH$_2$Cl$_2$/MeOH/NH$_4$OH: 97.5/2/0.5). The title product is obtained in the form of a translucent resin, which is dissolved directly in 40 ml of a mixture of CH$_3$CN/H$_2$O 50/50.

Conversion into a salt is then carried out using fumaric acid to yield the corresponding bis-fumarate, which is lyophilised: Melting point: 60–63° C.

Elemental Microanalysis

|  | C % | H % | N % |
|---|---|---|---|
| Theory: | 64.96 | 5.77 | 8.91 |
| Found: | 65.24 | 5.69 | 8.91 |

EXAMPLE 2

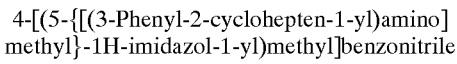
4-[(5-{[(3-Phenyl-2-cyclohepten-1-yl)amino]
methyl}-1H-imidazol-1-yl)methyl]benzonitrile The procedure is as for Example 1, in Step A replacing 1-bromo-2-methylbenzene by bromobenzene.

Conversion into a salt is carried out using fumaric acid to yield the corresponding fumarate:

Elemental Microanalysis

|  | C % | H % | N % |
|---|---|---|---|
| Theory: | 69.22 | 6.01 | 10.98 |
| Found: | 69.14 | 6.14 | 10.25 |

EXAMPLE 3

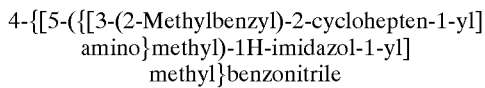
4-{[5-({[3-(2-Methylbenzyl)-2-cyclohepten-1-yl]
amino}methyl)-1H-imidazol-1-yl]
methyl}benzonitrile

Step A: tert-Butyl(dimethyl){[3-(2-methylbenzylidene)-1-cyclohepten-1-yl]oxy}silane

To a solution of cycloheptenone (71.7 mmol) in 220 ml of anhydrous THF there are added, in succession, triphenylphosphine (72.6 mmol) and then, dropwise, tert-butyldimethylsilyl triflate (72.3 mmol), and the whole is stirred at room temperature for 1 hour 30 minutes. The mixture is then brought to −78° C., and a solution of nBuLi/hexane (72 mmol) is added slowly, followed 30 minutes later by 2-methylbenzaldehyde (72.03 mmol). The whole is stirred at that temperature for 30 minutes, and then with the temperature gradually returning to room temperature. After 2 hours 30 minutes, the reaction mixture is precipitated from 2.5 liters of petroleum ether and filtered, and the filtrate is concentrated to dryness. The title product is purified by chromatography over silica gel (100% heptane).

Step B: (2-Methylbenzyl)-2-cyclohepten-1-one

A solution of n-tetra-n-butylammonium fluoride (1M) in THF (1.35 mmol) is added using a syringe to a solution of the compound obtained in Step A (1.34 mmol) in 15 ml of anhydrous THF at 0° C., and the whole is stirred at that temperature for 1 hour 30 minutes. The reaction mixture is then concentrated to dryness and deposited directly over a column of silica gel (heptane/AcOEt 9/1) to yield the title product.

**Step C: 4-{[5-({[3-(2-Methylbenzyl)-2-cyclohepten-1-yl]amino}methyl)-1H-imidazol-1-yl]
methyl}benzonitrile**

The title compound is obtained by coupling between the compound obtained in Preparation 2 (2 mmol) and the compound obtained in Step B (2 mmol) in the presence of Zn(BH$_4$)$_2$ (2 mmol) according to the method described in *J. Org. Chem.* 1998, 63, 370. The title product is obtained in pure form after purification over silica gel (CH$_2$Cl$_2$, MeOH, NH$_4$OH, 95/4/1), in the form of a translucent gum, which is converted to the fumarate salt.

EXAMPLE 4

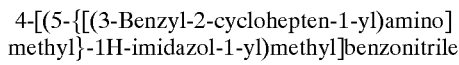
4-[(5-{[(3-Benzyl-2-cyclohepten-1-yl)amino]
methyl}-1H-imidazol-1-yl)methyl]benzonitrile The procedure is as for Example 3, in Step A replacing 2-methylbenzaldehyde by benzaldehyde.

EXAMPLE 5

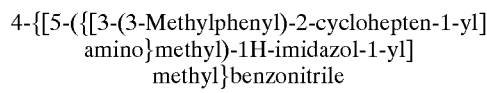
4-{[5-({[3-(3-Methylphenyl)-2-cyclohepten-1-yl]
amino}methyl)-1H-imidazol-1-yl]
methyl}benzonitrile The procedure is as for Example 1, in Step A replacing 1-bromo-2-methylbenzene by 1-bromo-3-methylbenzene.

Conversion into a salt is carried out using fumaric acid to yield the corresponding fumarate:

Elemental Microanalysis

|  | C % | H % | N % |
|---|---|---|---|
| Theory: | 70.29 | 6.29 | 10.93 |
| Found: | 70.39 | 6.06 | 10.90 |

EXAMPLE 6

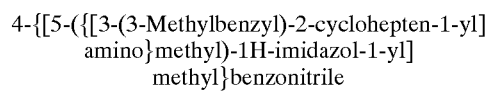
4-{[5-({[3-(3-Methylbenzyl)-2-cyclohepten-1-yl]
amino}methyl)-1H-imidazol-1-yl]
methyl}benzonitrile The procedure is as for Example 3, in Step A replacing 2-methylbenzaldehyde by 3-methylbenzaldehyde.

EXAMPLE 7

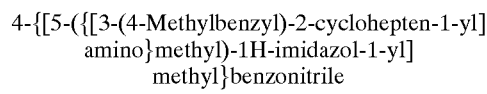
4-{[5-({[3-(4-Methylbenzyl)-2-cyclohepten-1-yl]
amino}methyl)-1H-imidazol-1-yl]
methyl}benzonitrile The procedure is as for Example 3, in Step A replacing 2-methylbenzaldehyde by 4-methylbenzaldehyde.

EXAMPLE 8

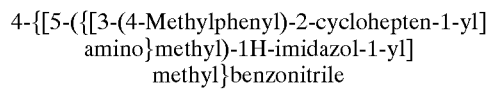
4-{[5-({[3-(4-Methylphenyl)-2-cyclohepten-1-yl]
amino}methyl)-1H-imidazol-1-yl]
methyl}benzonitrile The procedure is as for Example 1, in Step A replacing 1-bromo-2-methylbenzene by 1-bromo-4-methylbenzene.

Conversion into a salt is carried out using fumaric acid to yield the corresponding fumarate:

Elemental Microanalysis

|  | C % | H % | N % |
|---|---|---|---|
| Theory: | 70.29 | 6.29 | 10.93 |
| Found: | 70.31 | 6.08 | 10.88 |

EXAMPLE 9

4-{[5-({[3-(3-Chlorophenyl)-2-cyclohepten-1-yl]amino}methyl)-1H-imidazol-1-yl]methyl}benzonitrile The procedure is as for Example 1, in Step A replacing 1-bromo-2-methylbenzene by 1-bromo-3-chlorobenzene.
Elemental Microanalysis

|  | C % | H % | N % |
|---|---|---|---|
| Theory: | 61.30 | 5.56 | 11.44 |
| Found: | 61.77 | 5.58 | 11.26 |

EXAMPLE 10

4-{[5-({[3-(3-Chlorobenzyl)-2-cyclohepten-1-yl]amino}methyl)-1H-imidazol-1-yl]methyl}benzonitrile The procedure is as for Example 3, in Step A replacing 2-methylbenzaldehyde by 3-chlorobenzaldehyde.

EXAMPLE 11

4-{[5-({[3-(4-Chlorophenyl)-2-cyclohepten-1-yl]amino}methyl)-1H-imidazol-1-yl]methyl}benzonitrile The procedure is as for Example 1, in Step A replacing 1-bromo-2-methylbenzene by 1-bromo-4-chlorobenzene.

EXAMPLE 12

4-{[5-({[3-(4-Chlorobenzyl)-2-cyclohepten-1-yl]amino}methyl)-1H-imidazol-1-yl]methyl}benzonitrile The procedure is as for Example 3, in Step A replacing 2-methylbenzaldehyde by 4-chlorobenzaldehyde.

EXAMPLE 13

4-{[5-({[3-(2-Chlorophenyl)-2-cyclohepten-1-yl]amino}methyl)-1H-imidazol-1-yl]methyl}benzonitrile The procedure is as for Example 1, in Step A replacing 1-bromo-2-methylbenzene by 1-bromo-2-chlorobenzene.

EXAMPLE 14

4-{[5-({[3-(2-Chlorobenzyl)-2-cyclohepten-1-yl]amino}methyl)-1H-imidazol-1-yl]methyl}benzonitrile The procedure is as for Example 3, in Step A replacing 2-methylbenzaldehyde by 2-chlorobenzaldehyde.

EXAMPLE 15

4-{[5-({[3-(2,3-Dichlorophenyl)-2-cyclohepten-1-yl]amino}methyl)-1H-imidazol-1-yl]methyl}benzonitrile The procedure is as for Example 1, in Step A replacing 1-bromo-2-methylbenzene by 1-bromo-2,3-dichlorobenzene.

EXAMPLE 16

4-{[5-({[3-(2,3-Dichlorobenzyl)-2-cyclohepten-1-yl]amino}methyl)-1H-imidazol-1-yl]methyl}benzonitrile The procedure is as for Example 3, in Step A replacing 2-methylbenzaldehyde by 2,3-dichlorobenzaldehyde.

EXAMPLE 17

4-{[5-({[3-(2,4-Dichlorobenzyl)-2-cyclohepten-1-yl]amino}methyl)-1H-imidazol-1-yl]methyl}benzonitrile The procedure is as for Example 3, in Step A replacing 2-methylbenzaldehyde by 2,4-dichlorobenzaldehyde.

EXAMPLE 18

4-{[5-({[3-(2,4-Dichlorophenyl)-2-cyclohepten-1-yl]amino}methyl)-1H-imidazol-1-yl]methyl}benzonitrile The procedure is as for Example 1, in Step A replacing 1-bromo-2-methylbenzene by 1-bromo-2,4-dichlorobenzene.

EXAMPLE 19

4-{[5-({[3-(2,5-Dichlorophenyl)-2-cyclohepten-1-yl]amino}methyl)-1H-imidazol-1-yl]methyl}benzonitrile The procedure is as for Example 1, in Step A replacing 1-bromo-2-methylbenzene by 1-bromo-2,5-dichlorobenzene.

EXAMPLE 20

4-{[5-({[3-(2,5-Dichlorobenzyl)-2-cyclohepten-1-yl]amino}methyl)-1H-imidazol-1-yl]methyl}benzonitrile The procedure is as for Example 3, in Step A replacing 2-methylbenzaldehyde by 2,5-dichlorobenzaldehyde.

EXAMPLE 21

4-{[5-({[3-(3,5-Dichlorobenzyl)-2-cyclohepten-1-yl]amino}methyl)-1H-imidazol-1-yl]methyl}benzonitrile The procedure is as for Example 3, in Step A replacing 2-methylbenzaldehyde by 3,5-dichlorobenzaldehyde.

EXAMPLE 22

4-{[5-({[3-(3,5-Dichlorophenyl)-2-cyclohepten-1-yl]amino}methyl)-1H-imidazol-1-yl]methyl}benzonitrile The procedure is as for Example 1, in Step A replacing 1-bromo-2-methylbenzene by 13-bromo-3,5-dichlorobenzene.

EXAMPLE 23

4-{[5-({[3-(3,4-Dichlorobenzyl)-2-cyclohepten-1-yl]amino}methyl)-1H-imidazol-1-yl]methyl}benzonitrile The procedure is as for Example 3, in Step A replacing 2-methylbenzaldehyde by 3,4-dichlorobenzaldehyde.

EXAMPLE 24

4-{[5-({[3-(3,4-Dichlorophenyl)-2-cyclohepten-1-yl]amino}methyl)-1H-imidazol-1-yl]methyl}benzonitrile The procedure is as for Example 1, in Step A replacing 1-bromo-2-methylbenzene by 1-bromo-3,4-dichlorobenzene.

EXAMPLE 25

4-{[5-({[3-(2,3-Dichlorophenyl)-2-cyclohepten-1-yl]amino}methyl)-1H-imidazol-1-yl]methyl)}benzonitrile The procedure is as for Example 1, in Step A replacing 1-bromo-2-methylbenzene by 1-bromo-2,3-dichlorobenzene.

EXAMPLE 26

4-{[5-({[3-(2,3-Dichlorobenzyl)-2-cyclohepten-1-yl]amino}methyl)-1H-imidazol-1-yl]methyl}benzonitrile The procedure is as for Example 3, in Step A replacing 2-methylbenzaldehyde by 2,3-dichlorobenzaldehyde.

EXAMPLE 27

4-{[5-({[3-(4-Chloro-2-methylphenyl)-2-cyclohepten-1-yl]amino}-methyl)-1H-imidazol-1-yl]methyl)}benzonitrile The procedure is as for Example 1, in Step A replacing 1-bromo-2-methylbenzene by 1-bromo-4-chloro-2-methylbenzene.

EXAMPLE 28

4-{[5-({[3-(4-Fluoro-2-methylphenyl)-2-cyclohepten-1-yl]amino}-methyl)-1H-imidazol-1-yl]methyl}benzonitrile The procedure is as for Example 1, in Step A replacing 1-bromo-2-methylbenzene by 1-bromo-4-fluoro-2-methylbenzene.

EXAMPLE 29

4-{[5-({[3-(2,4-Dimethylphenyl)-2-cyclohepten-1-yl]amino}methyl)-1H-imidazol-1-yl]methyl}benzonitrile The procedure is as for Example 1, in Step A replacing 1-bromo-2-methylbenzene by 1-bromo-2,4-dimethylbenzene.

EXAMPLE 30

4-{1-[5-({[3-(2-Methylphenyl)-2-cyclohepten-1-yl]amino}methyl)-1H-imidazol-1-yl]ethyl}benzonitrile The procedure is as for Example 1, in Step F replacing the compound obtained in Preparation 1 by the compound obtained in Preparation 3.

EXAMPLE 31

4-{[3-({[3-(2-Methylphenyl)-2-cyclohepten-1-yl]amino}methyl)-4-pyridyl]methyl}benzonitrile The procedure is as for Example 1, in Step F replacing the compound obtained in Preparation 1 by the compound obtained in Preparation 14.

Conversion into a salt is carried out using fumaric acid to yield the corresponding bis-fumarate:
Elemental Microanalysis

|  | C % | H % | N % |
|---|---|---|---|
| Theory: | 67.59 | 5.83 | 6.57 |
| Found: | 67.04 | 5.72 | 6.07 |

EXAMPLE 32

4-{[5-({[3-(2-Methylphenyl)-2-cyclohepten-1-yl]amino}methyl)-1H-imidazol-1-yl]methyl}cyclohexanecarbonitrile The procedure is as for Example 1, in Step F replacing the compound obtained in Preparation 1 by the compound obtained in Preparation 4.

EXAMPLE 33

N-({1-[(1-Cyano-4-piperidyl)methyl]-1H-imidazol-5-yl}methyl)-N-[3-(2-methylphenyl)-2-cyclohepten-1-yl]amine The procedure is as for Example 1, in Step F replacing the compound obtained in Preparation 1 by the compound obtained in Preparation 5.

EXAMPLE 34

4-{[5-({[3-(3-Methylphenyl)-2-cyclohepten-1-yl]amino}methyl)-1H-imidazol-1-yl]methyl}cyclohexanecarbonitrile The procedure is as for Example 1, in Step A replacing 1-bromo-2-methylbenzene by 1-bromo-3-methylbenzene and in Step F replacing the compound obtained in Preparation 1 by the compound obtained in Preparation 4.

EXAMPLE 35

N-({1-[(1-Cyano-4-piperidyl)methyl]-1H-imidazol-5-yl}methyl)-N-[3-(3-methylphenyl)-2-cyclohepten-1-yl]amine The procedure is as for Example 1, in Step A replacing 1-bromo-2-methylbenzene by 1-bromo-3-methylbenzene and in Step F replacing the compound obtained in Preparation 1 by the compound obtained in Preparation 5.

EXAMPLE 36

4-{[5-({[3-(2-Chlorophenyl)-2-cyclohepten-1-yl]amino}methyl)-1H-imidazol-1-yl]methyl}cyclohexanecarbonitrile The procedure is as for Example 1, in Step A replacing 1-bromo-2-methylbenzene by 1-bromo-2-chlorobenzene and in Step F replacing the compound obtained in Preparation 1 by the compound obtained in Preparation 4.

EXAMPLE 37

4-{[5-({[3-(3-Chlorophenyl)-2-cyclohepten-1-yl]amino}methyl)-1H-imidazol-1-yl]methyl}cyclohexanecarbonitrile The procedure is as for Example 1, in Step A replacing 1-bromo-2-methylbenzene by 1-bromo-3-chlorobenzene and in Step F replacing the compound obtained in Preparation 1 by the compound obtained in Preparation 4.

EXAMPLE 38

N-({1-[(1-Cyano-4-piperidyl)methyl]-1H-imidazol-5-yl}methyl)-N-[3-(3-chlorophenyl)-2-cyclohepten-1-yl]amine The procedure is as for Example 1, in Step A replacing 1-bromo-2-methylbenzene by 1-bromo-2-chlorobenzene and in Step F replacing the compound obtained in Preparation 1 by the compound obtained in Preparation 5.

EXAMPLE 39

N-({1-[(1-Cyano-4-piperidyl)methyl]-1H-imidazol-5-yl}methyl)-N-[3-(3-chlorophenyl)-2-cyclohepten-1-yl]amine The procedure is as for Example 1, in Step A replacing 1-bromo-2-methylbenzene by 1-bromo-3-chlorobenzene and in Step F replacing the compound obtained in Preparation 1 by the compound obtained in Preparation 5.

EXAMPLE 40

4-[(5-{[(3-Mesityl-2-cyclohepten-1-yl)amino]methyl}-1H-imidazol-1-yl)methyl]benzonitrile The procedure is as for Example 1, in Step A replacing 1-bromo-2-methylbenzene by 1-bromo-2,4,6-trimethylbenzene.
Conversion into a salt is carried out using fumaric acid to yield the corresponding bis-fumarate:
Elemental Microanalysis

|  | C % | H % | N % |
|---|---|---|---|
| Theory: | 65.84 | 6.14 | 8.53 |
| Found: | 65.48 | 6.07 | 8.48 |

EXAMPLE 41

4-({5-[({3-[(Phenylthio)methyl]-2-cyclohepten-1-yl}amino)methyl]-1H-imidazol-1-yl}methyl)benzonitrile The procedure is as for Example 1, in Step A replacing 1-bromo-2-methylbenzene by [(bromomethyl)thio]benzene.
Conversion into a salt is carried out using fumaric acid to yield the corresponding bis-fumarate:
Elemental Microanalysis

|  | C % | H % | N % | S % |
|---|---|---|---|---|
| Theory: | 61.81 | 5.49 | 8.48 | 4.85 |
| Found: | 61.99 | 5.76 | 8.45 | 4.82 |

EXAMPLE 42

N-{3-[(Phenylthio)methyl]-2-cyclohepten-1-yl}-N-(3-pyridyl-methyl)amine

The procedure is as for Example 1, in Step A replacing 1-bromo-2-methylbenzene by [(bromomethyl)thio]benzene and in Step F replacing the compound obtained in Preparation 1 by nicotinaldehyde.
Conversion into a salt is carried out using fumaric acid to yield the corresponding bis-fumarate:
Elemental Microanalysis

|  | C % | H % | N % | S % |
|---|---|---|---|---|
| Theory: | 60.42 | 5.79 | 5.03 | 5.76 |
| Found: | 60.51 | 5.85 | 4.89 | 5.60 |

EXAMPLE 43

4-{[{3-[(Phenylthio)methyl]-2-cyclohepten-1-yl}(3-pyridylmethyl)-amino]methyl}benzonitrile The procedure is as for Step F of Example 1, starting from the compound obtained in Example 42, replacing the compound obtained in Preparation 1 by 4-formylbenzonitrile.
Conversion into a salt is carried out using fumaric acid to yield the corresponding bis-fumarate:
Elemental Microanalysis

|  | C % | H % | N % | S % |
|---|---|---|---|---|
| Theory: | 65.19 | 5.63 | 6.48 | 4.94 |
| Found: | 65.35 | 5.83 | 6.58 | 4.92 |

EXAMPLE 44

N-[(1-Benzyl-1H-imidazol-5-yl)methyl]-N-[3-(2-methylphenyl)-2-cyclohepten-1-yl]amine The procedure is as for Example 1, in Step F replacing the compound obtained in Preparation 1 by the compound obtained in Preparation 11.

EXAMPLE 45

N-[3-(2-Methylphenyl)-2-cyclohepten-1-yl]-N-{[1-(2-phenylethyl)-1H-imidazol-5-yl]methyl} amine The procedure is as for Example 1, in Step F replacing the compound obtained in Preparation 1 by the compound obtained in Preparation 13.

EXAMPLE 46

N-[3-(2-Methylphenyl)-2-cyclohepten-1-yl]-N-{[1-(3-phenylpropyl)-1H-imidazol-5-yl]methyl}amine The procedure is as for Example 1, in Step F replacing the compound obtained in Preparation 1 by the compound obtained in Preparation 6.

EXAMPLE 47

N-{[1-(4-Chlorobenzyl)-1H-imidazol-5-yl]methyl}-N-[3-(2-methylphenyl)-2-cyclohepten-1-yl]amine The procedure is as for Example 1, in Step F replacing the compound obtained in Preparation 1 by the compound obtained in Preparation 8.

EXAMPLE 48

N-{[1-(3-Chlorobenzyl)-1H-imidazol-5-yl]methyl}-N-[3-(2-methylphenyl)-2-cyclohepten-1-yl]amine The procedure is as for Example 1, in Step F replacing the compound obtained in Preparation 1 by the compound obtained in Preparation 9.

EXAMPLE 49

N-{[1-(4-Bromobenzyl)-1H-imidazol-5-yl]methyl}-
N-[3-(2-methylphenyl)-2-cyclohepten-1-yl]amine The procedure is as for Example 1, in Step F replacing the compound obtained in Preparation 1 by the compound obtained in Preparation 10.

EXAMPLE 50

N-[(1-Benzyl-1H-imidazol-5-yl)methyl]-N-(3-phenyl-2-cyclohepten-1-yl)amine

The procedure is as for Example 1, in Step A replacing 1-bromo-2-methylbenzene by bromobenzene and in Step F replacing the compound obtained in Preparation 1 by the compound obtained in Preparation 11.

EXAMPLE 51

N-[(1-Benzyl-1H-imidazol-5-yl)methyl]-N-[3-(3-chlorophenyl)-2-cyclohepten-1-yl]amine The procedure is as for Example 1, in Step A replacing 1-bromo-2-methylbenzene by 1-bromo-3-chlorobenzene and in Step F replacing the compound obtained in Preparation 1 by the compound obtained in Preparation 11.

EXAMPLE 52

N-{[1-(4-Fluorobenzyl)-1H-imidazol-5-yl]methyl}-
N-(3-phenyl-2-cyclohepten-1-yl)amine The procedure is as for Example 1, in Step A replacing 1-bromo-2-methylbenzene by bromobenzene and in Step F replacing the compound obtained in Preparation 1 by the compound obtained in Preparation 7.

EXAMPLE 53

N-{[1-(4-Chlorobenzyl)-1H-imidazol-5-yl]methyl}-
N-[3-(2-chlorophenyl)-2-cyclohepten-1-yl]amine The procedure is as for Example 1, in Step A replacing 1-bromo-2-methylbenzene by 1-bromo-2-chlorobenzene and in Step F replacing the compound obtained in Preparation 1 by the compound obtained in Preparation 8.

EXAMPLE 54

N-{[1-(3-Chlorobenzyl)-1H-imidazol-5-yl]methyl}-
N-[3-(3-chlorophenyl)-2-cyclohepten-1-yl]amine The procedure is as for Example 1, in Step A replacing 1-bromo-2-methylbenzene by 1-bromo-3-chlorobenzene and in Step F replacing the compound obtained in Preparation 1 by the compound obtained in Preparation 9.

EXAMPLE 55

4-{[3-({[3-(3-Chlorophenyl)-2-cyclohepten-1-yl]amino}methyl)-4-pyridyl]methyl}benzonitrile The procedure is as for Example 1, in Step A replacing 1-bromo-2-methylbenzene by 1-bromo-2-chlorobenzene and in Step F replacing the compound obtained in Preparation 1 by the compound obtained in Preparation 14.

EXAMPLE 56

N-{3-[(Phenylthio)methyl]-2-cyclohepten-1-yl}-N,N-bis(3-pyridyl-methyl)amine

The procedure is as for Step F of Example 1 starting from the compound obtained in Example 42, replacing the compound obtained in Preparation 1 by nicotinaldehyde.

EXAMPLE 57

4-{[5-(2-{[3-(3-Chlorophenyl)-2-cyclohepten-1-yl]amino}ethyl)-1H-imidazol-1-yl]methyl}benzonitrile The procedure is as for Example 1, in Step A replacing 1-bromo-2-methylbenzene by 1-bromo-3-chlorobenzene and in Step F replacing the compound obtained in Preparation 1 by the compound obtained in Preparation 12.

EXAMPLE 58

4-[{[3-(3-Chlorophenyl)-2-cyclohepten-1-yl]amino}(1H-imidazol-5-yl)methyl]benzonitrile The procedure is as for Example 1, in Step A replacing 1-bromo-2-methylbenzene by 1-bromo-3-chlorobenzene and in Step F replacing the compound obtained in Preparation 1 by the compound obtained in Preparation 15.

EXAMPLE 59

4-[{[3-(3-Chlorophenyl)-2-cyclohepten-1-yl]amino}(1-methyl-1H-imidazol-5-yl)methyl]benzonitrile The procedure is as for Example 1, in Step A replacing 1-bromo-2-methylbenzene by 1-bromo-3-chlorobenzene and in Step F replacing the compound obtained in Preparation 1 by the compound obtained in Preparation 16.

EXAMPLE 60

4-[2-{[3-(3-Chlorophenyl)-2-cyclohepten-1-yl]amino}-2-(1H-imidazol-5-yl)ethyl]benzonitrile The procedure is as for Example 1, in Step A replacing 1-bromo-2-methylbenzene by 1-bromo-3-chlorobenzene and in Step F replacing the compound obtained in Preparation 1 by the compound obtained in Preparation 17.

EXAMPLE 61

4-[2-{[3-(3-Chlorophenyl)-2-cyclohepten-1-yl]amino}-2-(1-methyl-1H-imidazol-5-yl)ethyl]benzonitrile The procedure is as for Example 1, in Step A replacing 1-bromo-2-methylbenzene by 1-bromo-3-chlorobenzene and in Step F replacing the compound obtained in Preparation 1 by the compound obtained in Preparation 18.

EXAMPLE 62

3-(3-Chlorophenyl)-N-[(4-chlorophenyl)(1H-imidazol-5-yl)methyl]-2-cyclohepten-1-amine The procedure is as for Example 1, in Step A replacing 1-bromo-2-methylbenzene by 1-bromo-3-chlorobenzene and in Step F replacing the compound obtained in Preparation 1 by the compound obtained in Preparation 19.

EXAMPLE 63

3-(3-Chlorophenyl)-N-[(4-chlorophenyl)(1-methyl-1H-imidazol-5-yl)methyl]-2-cyclohepten-1-amine The procedure is as for Example 1, in Step A replacing 1-bromo-2-methylbenzene by 1-bromo-3-chlorobenzene and in Step F replacing the compound obtained in Preparation 1 by the compound obtained in Preparation 20.

EXAMPLE 64

3-(3-Chlorophenyl)-N-[2-(4-chlorophenyl-1-(1H-imidazol-5-yl)ethyl]-2-cyclohepten-1-amine The procedure is as for Example 1, in Step A replacing 1-bromo-2-methylbenzene by 1-bromo-3-chlorobenzene and in Step F replacing the compound obtained in Preparation 1 by the compound obtained in Preparation 21.

EXAMPLE 65

3-(3-Chlorophenyl)-N-[2-(4-chlorophenyl)-1-(1-methyl-1H-imidazol-5-yl)ethyl]-2-cyclohepten-1-amine The procedure is as for Example 1, in Step A replacing 1-bromo-2-methylbenzene by 1-bromo-3-chlorobenzene and in Step F replacing the compound obtained in Preparation 1 by the compound obtained in Preparation 22.

Pharmacological Study

Example A

Enzyme Tests

The two enzymes FTase and GGTase-I were purified starting from rat's brain. After grinding and centrifuging, the supernatant is precipitated with 30% ammonium sulphate and the resulting supernatant is subjected to another precipitation with 50% ammonium sulphate. The pellet is then passed through a column of phenyl agarose and the fractions collected after elution with sodium chloride are evaluated for their enzyme content in accordance with the "scintillation proximity assay" method described hereinbelow. The fractions corresponding to one or other of the two enzymes are then combined and frozen at −80° C. until use.

The determination of the enzymatic activity of the FTase is carried out in 96-well plates by a radioactive scintillation proximity assay method. The acceptor substrate composed of the carboxy-terminal sequence of lamin B (YRASNRSCAIM) coupled to biotin is incubated in the presence of the radiolabelled donor substrate ([$^3$H]farnesyl pyrophosphate), and of various concentrations of test compounds in DMSO. The reaction is initiated at 37° C. by adding FTase enzyme for a duration of one hour, and is then stopped with an appropriate buffer containing a suspension of beads impregnated with scintillant. Those beads are in addition coupled to streptavidin in order to capture, by coupling to biotin, the peptide susceptible to farnesylation, and hence place the radiolabelled farnesyl group in contact with the scintillant. The plates are read in a radioactivity counter and the data are converted into percentages of a control in order to express the results in the form of the concentration of test product that causes 50% inhibition of farnesylation ($IC_{50}$).

For GGTase-I an equivalent test was used, replacing the acceptor substrate with the biotinylated sequence TKCVIL and replacing the donor substrate with [$^3$H]geranylgeranyl pyrophosphate.

Results

The compounds of the present invention have $IC_{50}$s of the order of nanomolar with respect to FTase, revealing their character as powerful inhibitors of that enzyme, and demonstrate an appreciable selectivity in comparison with GGTase-I, the $IC_{50}$s in that case being only of the order of micromolar.

Example B

Cell Proliferation Tests a) The RAT2 line of rat fibroblasts and an appropriate transfectant for the insertion of the gene v-H-ras were used to test the effectiveness of the claimed products on cells. The RAT2 cells allow the intrinsic toxicity of the test product to be characterised, while the transfected cells that exhibit a changed morphology and a more rapid growth rate serve to measure the desired specific effect on intracellular FTase.

The parental and transfected cells are cultured in 96-well plates for cell culture in the presence of medium containing 10% serum. Twenty four hours later, the test products are added to the same medium over a period of four days and the final quantity of cells is estimated indirectly by the cell viability method using 3-(4,5-dimethylthiazol-2-yl)-2,5-diphenyltetrazolium bromide (MTT).

Results

In the case of the compounds of the invention, a slow-down in the growth of cells transfected with v-H-ras is observed in the nanomolar range. That effect, reflecting the return of the transfected cells to the growth characteristics of the parental line, is accompanied also by a reversion of the morphology of the transfectants to the parental phenotype (spread, and loss of refraction). Several logarithmic units separate that specific effect from the cytotoxic effect observed on the RAT2 cells in the micromolar range, the most favourable differential being at least four units for the most active products.

a) Complementary tests on human carcinoma lines obtained from clinical biopsies are carried out. The lines used all come from the ATCC (American Type Culture Collection) and the test is carried out in 96-well plates for a duration of contact with the product corresponding to four doubling periods.

Results

Observation under a microscope and an indirect count by the MTT method allowed an anti-proliferative activity to be demonstrated with $IC_{50}$s of the order of a hundred nanomolar in the case of the compounds of the invention on the line EJ138, a bladder carcinoma exhibiting a mutation of the H-Ras protein. The inhibition is accompanied by an effect on the morphology of the cells similar to that observed on the rat v-H-ras transfectants.

Example C

Ras Protein in vitro Prenylation Test

Rat fibroblast cells transfected with v-H-ras, and EJ138 vesical carcinoma cells exhibiting an H-Ras mutation, are cultured at high density and then treated twenty four hours later and for forty eight hours with different concentrations of the test compounds. The cell lysates are deposited on an electrophoresis gel and the separated proteins are transferred for use in a Western blot with an antibody directed against the Ras protein recognising prenylated or non-prenylated forms.

Results

With the compounds of the invention, a modification of the farnesylation of Ras with a halved effect of the order of 10 nM is observed, concurring with their effectiveness on the purified FTase enzyme.

Example D

Growth Test in Agar

The cells are cultured in the presence of serum and various concentrations of the test compounds in agar in order to evaluate their growth independently of the substrate. Under those so-called clonogenic growth conditions, the RAT2 cells remain as isolated and viable cells for the duration of the experiment (two weeks). Conversely, the cells transfected with v-H-ras form multi-cellular colonies which can be counted and the size of which can be measured by image analysis.

Results

The compounds of the invention inhibit the formation of aggregates with an $IC_{50}$ of the order of 10 nM without exerting a cytotoxic effect, since the majority of the transfected cells treated with concentrations higher than the $IC_{50}$ remain in the form of isolated and viable cells like the untreated parental RAT2 cells.

Example E

In vitro Angiogenesis Test

This test comprises culturing fragments of rat aorta in a three-dimensional collagen gel, in a perfectly defined medium and without serum, in accordance with a method described in *Lab Invest* 1990, 63, 115–122. From the third day of the culture, a vascular arborisation develops, preceded by an appreciable emigration of individualised fibroblasts.

Results

Under those culture conditions and after five days' contact with the compounds of the invention, a selective effect on the inhibition of cellular excrescence is observed: only endothelial cells are affected with an $IC_{50}$ of the order of a hundred nanomolar.

Example F

Pharmaceutical Composition

Formulation for the preparation of 1000 tablets each comprising 10 mg of active ingredient

| | |
|---|---|
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

What is claimed is:
1. A Compound of formula (I):

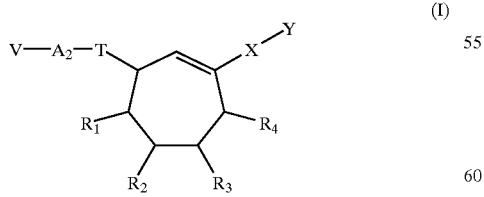

wherein:
X may be a bond or a group selected from alkylene, CO, $S(O)_n$, *—$S(O)_n$—$A_1$—, *—CO—$A_1$—, —$A_1$—$S(O)_n$—$A'_1$— and —$A_1$—CO—$A'_1$— (wherein $A_1$ and $A'_1$, which may be identical or different, represent alkylene and n is 0, 1 or 2), the symbol "*" indicating the point of attachment of those groups to the cycloheptene, Y is selected from aryl, heteroaryl, cycloalkyl and heterocycloalkyl, each of those groups being unsubstituted or substituted by one or more, identical or different, $R_8$ groups, $R_1$, $R_2$, $R_3$ and $R_4$ independently represent hydrogen or aryl, heteroaryl, cycloalkyl or heterocycloalkyl, each of those groups being unsubstituted or substituted by one or more, identical or different, $R_8$ groups.

or $R_1$, $R_2$, $R_3$ and $R_4$, taken in pairs, together form a bond, or $R_1$ and $R_2$, or $R_2$ and $R_3$, or $R_3$ and $R^4$, taken in pairs with the carbon atoms to which they are bonded, form fused benzene or a fused aromatic or partially unsaturated heterocycle, having 5 or 6 ring members and containing 1 or 2 hetero atoms selected from nitrogen, oxygen and sulphur, with the understanding that only one ring can be fused on the 7-membered structure, T is selected from —CH($R_5$)—, —N($R_5$)— and *—N($R_5$)CO— (wherein $R_5$ is selected from hydrogen, alkyl, aryl, heteroaryl, arylalkyl and heteroarylalkyl, each of those groups being unsubstituted or substituted by one or more, identical or different, $R_7$ groups), the symbol "*" indicating the point of attachment of the group to the cycloheptene, V is selected from hydrogen, aryl, and heteroaryl, each of those groups being unsubstituted or substituted by one or more, identical or different, $R_7$ groups, $A_2$ may be $[C(R_6)(R'_6)]_p$ wherein p is 0, 1, 2, 3 or 4 when T represents —CH($R_5$)— or *—N($R_5$)CO—, or p is 1, 2, 3 or 4 when T represents —N($R_5$)—; and $R_6$ and $R'_6$, which may be identical or different, represent hydrogen or alkyl, alkenyl, alkynyl, optionally substituted aryl, optionally substituted heteroaryl, optionally substituted heterocycloalkyl, optionally substituted arylalkyl, optionally substituted heteroarylalkyl or optionally substituted heterocycloalkylalkyl group, $R_9$ or alkyl substituted by $R_9$ (wherein $R_9$ represents —$OR_5$, —N($R_5$)($R'_5$), —S(O)$R_5$, —CON($R_5$)($R'_5$), —N($R_5$)COR'$_5$, —N($R_5$)$SO_2R'_5$, —$SO_2N(R_5)(R'_5)$ or —N($R_5$)COO(R'5), m being 0, 1 or 2, and $R'_5$ can have any of the meanings of $R_5$), $R_7$ may be halogen or alkyl, alkoxy, hydroxy, mercapto, alkylthio, cyano, amino (optionally substituted by one or two alkyl groups), nitro, carboxy, alkoxycarbonyl, aminocarbonyl (optionally substituted by one or two alkyl groups), carbamoyl, unsubstituted or substituted aryl, unsubstituted or substituted arylalkyl, unsubstituted or substituted heteroaryl, unsubstituted or substituted heteroarylalkyl, unsubstituted or substituted cycloalkyl, unsubstituted or substituted cycloalkylalkyl, unsubstituted or substituted heterocycloalkyl or unsubstituted or substituted heterocycloalkylalkyl group, $R_8$ may be halogen, or oxo, hydroxy, cyano, nitro, carboxy, alkoxycarbonyl or perhaloalkyl or —U-$R_{80}$ or —$A_{80}$-U—$R_{80}$ (wherein $A_{80}$ represents alkylene; U represents a bond, oxygen or a group selected from NH, $S(O)_m$, NHCO, CONH, $SO_2NH$ and $NHSO_2$, m being 0, 1 or 2; and $R_{80}$ is a group selected from alkyl, aryl, arylalkyl, heteroaryl and heteroarylalkyl), it being understood that:

the term "alkyl" denotes a linear or branched group containing from 1 to 6 carbon atoms, the term "alkylene" denotes a linear or branched bivalent group containing from 1 to 6 carbon atoms, the term "cycloalkyl" denotes a saturated cyclic group containing from 3 to 8 carbon atoms, the term "heterocycloalkyl" denotes a saturated or partially unsaturated cyclic group having from 5 to 7 ring members and containing from 1 to 3 hetero atoms selected from nitrogen, oxygen and sulphur, the term "aryl" denotes a phenyl or naphthyl group, the term "heteroaryl" denotes a mono- or bi-cyclic group that is aromatic or contains at least one aromatic ring, has from 5 to 11 ring members and contains from 1 to 5 hetero atoms selected from nitrogen, oxygen and sulphur, the term "substituted" applied to the terms "aryl", "heteroaryl", "cycloalkyl" and "heterocycloalkyl" means that those groups may be substituted by one or more identical or different groups selected from cyano, alkylcarbonyl, aminocarbonyl (optionally substituted by one or two alkyl groups) and halogen atoms, the term "substituted" applied to the terms "arylalkyl", "heteroarylalkyl", "cycloalkylalkyl" and "heterocycloalkylalkyl" means that the cyclic moiety of those groups may be substituted by one or more identical or different groups selected from oxo, cyano, alkylcarbonyl, aminocarbonyl (optionally substituted by one or two alkyl groups) and halogen atoms, provided that when T is $N(R_5)$, then $R^1$, $R^2$, $R^3$, and $R_4$, taken in pairs, may not together form a bond, its enantiomers, diastereoisomers, and addition salts thereof with a pharmaceutically acceptable acid or base.

2. A compound of claim 1, wherein X represents a bond.

3. A compound of claim 1, wherein Y represents aryl optionally substituted by $R_8$.

4. A compound of claim 1, wherein each of $R_1$, $R_2$, $R_3$ and $R_4$ represents hydrogen.

5. A compound of claim 1, wherein T represents $—N(R_5)—$.

6. A compound of claim 5, wherein T represents —NH.

7. A compound of claim 1, wherein $A_2$ represents a $—CH_2—$ or $—CH_2—CH_2—$ group.

8. A compound of claim 1, wherein $A_2$ represents (4-cyano-phenyl)methylene, (4-chlorophenyl)methylene, (4-cyanobenzyl)methylene or (4-chloro-benzyl)methylene.

9. A compound of claim 1, wherein V represents heteroaryl optionally substituted by $R_7$.

10. A compound of claim 1, wherein V represents imidazolyl optionally substituted by $R_7$.

11. A compound of claim 9, wherein $R_7$ represents unsubstituted or substituted arylalkyl or unsubstituted substituted heteroaryl.

12. A compound of claim 10, wherein $R_7$ represents unsubstituted or substituted arylalkyl or unsubstituted or substituted heteroaryl.

13. A compound of claim 1, wherein X represents a bond; Y represents aryl optionally substituted by $R_8$; each of $R_1$, $R_2$, $R_3$ and $R_4$ represents hydrogen; T represents —NH—; $A_2$ represents $—CH_2—$, $—CH_2—CH_2—$, (4-cyanophenyl)methylene, (4-chlorophenyl)methylene, (4-cyanobenzyl)methylene or (4-chlorobenzyl)methylene; and V represents heteroaryl optionally substituted by $R_7$.

14. A compound of claim 1, wherein X represents a bond; Y represents aryl optionally substituted by $R_8$; each of $R_1$, $R_2$, $R_3$ and $R_4$ represents hydrogen; T represents —NH—; $A_2$ represents $—CH_2—$, $—CH_2—CH_2$ —, (4-cyanophenyl)methylene, (4-chlorophenyl)methylene, (4-cyanobenzyl)methylene or (4-chlorobenzyl)methylene; and V represents imidazolyl optionally substituted by $R_7$.

15. A compound of claim 1 selected from (R,S)-4-{[5-({[3-(2-methylphenyl)-2-cyclohepten-1-yl]amino}methyl)-1H-imidazol-1-yl]methyl}benzonitrile, 4-{[5-({[3-(3-methylphenyl)-2-cyclohepten-1-yl]amino}methyl)-1H-imidazol-1-yl]-methyl}benzonitrile, and 4-{[5-({[3-(3-chlorophenyl)-2-cyclohepten-1-yl]amino}methyl)-1H-imidazol-1-yl]methyl}benzonitrile.

16. A pharmaceutical composition useful in treating an animal or human living body afflicted with a condition requiring a farnesyl transferase inhibitor comprising as active principle an effective amount of a compound as claimed in claim 1, together with one or more pharmaceutically acceptable excipients or vehicles.

17. A pharmaceutical composition useful in treating an animal or human living body afflicted with a condition requiring treatment of cancerous diseases comprising as active principle an effective amount of a compound as claimed in claim 1, together with one or more pharmaceutically acceptable excipients or vehicles.

18. A pharmaceutical composition useful in treating an animal or human living body afflicted with a condition requiring treatment of restinosis after angioplasty or vascular surgery, and type I neurofibromatosis comprising as active principle an effective amount of a compound as claimed in claim 1, together with one or more pharmaceutically acceptable excipients or vehicles.

19. A method for treating an animal or human living body afflicted with a condition requiring a farnesyl transferase inhibitor comprising the step of administering to the living body an amount of a compound of claim 1 which is effective for alleviation of said condition.

20. A method for treating an animal or human living body afflicted with a condition requiring treatment of cancerous diseases comprising the step of of administering to the living body an amount of a compound of claim 1 which is effective for alleviation of said condition.

21. A method for treating an animal or human living body afflicted with a condition requiring treatment of restinosis after angioplasty or vascular surgery, and type I neurofibromatosis comprising the step of of administering to the living body an amount of a compound of claim 1 which is effective for alleviation of said condition.

* * * * *

UNITED STATES PATENT AND TRADEMARK OFFICE
CERTIFICATE OF CORRECTION

PATENT NO. : 6,638,962 B2
DATED : October 28, 2003
INVENTOR(S) : Patrick Casara et al.

It is certified that error appears in the above-identified patent and that said Letters Patent is hereby corrected as shown below:

Column 28,
Line 14, "$R^4$" should be -- $R_4$ --.
Line 43, "-$S(O)R_5$", should be -- -$S(O)_m R_5$ --.
Line 45, "($R'5$)", should be -- ($R_5$) --.

Column 29,
Line 33, "$R^1, R^2, R^3,$" should be -- $R_1, R_2, R_3,$ --.

Signed and Sealed this

Twenty-third Day of March, 2004

JON W. DUDAS
*Acting Director of the United States Patent and Trademark Office*